United States Patent [19]

Hansen et al.

[11] Patent Number: 5,658,899
[45] Date of Patent: Aug. 19, 1997

[54] ACID ADDITION SALTS OF 2, 3, 4, 5-TETRAHYDRO-1H-3-BENZAZEPINE COMPOUNDS

[75] Inventors: Louis Brammer Hansen, Værløse; Rolf Emil Amsler, Allerød; Scott Eugene McGraw, Stenløse, all of Denmark

[73] Assignee: Novo Nordisk A/S, Bagsvaerd, Denmark

[21] Appl. No.: 404,394

[22] Filed: Mar. 14, 1995

[30] Foreign Application Priority Data

Mar. 26, 1994 [DK] Denmark ................ 0311/94

[51] Int. Cl.⁶ ................ A61K 31/55; C07D 233/16
[52] U.S. Cl. ................ 514/213; 540/595; 549/462
[58] Field of Search ................ 540/595; 549/462; 514/213

[56] References Cited

U.S. PATENT DOCUMENTS

5,470,850  11/1995  Foged et al. ................ 514/213

FOREIGN PATENT DOCUMENTS

WO93/17012  2/1993  WIPO.
17012  9/1993  WIPO.

OTHER PUBLICATIONS

Kaiser et al., J. Med. Chem., vol. 25, No. 6, pp. 697–703 (1982).

*Primary Examiner*—Johann Richter
*Assistant Examiner*—Richard S. Myers, Jr.
*Attorney, Agent, or Firm*—Steve T. Zelson; Cheryl H. Agris

[57] ABSTRACT

The invention provides a series of crystalline salts of (S)-8-chloro-5-(5-bromo-2,3-dihydrobenzofuran-7-yl)-3-methyl-2,3,4,5-tetrahydro-1H-3-benzazepine-7-ol, their preparation and use as therapeutic agents.

6 Claims, No Drawings

ACID ADDITION SALTS OF 2, 3, 4, 5-TETRAHYDRO-1H-3-BENZAZEPINE COMPOUNDS

The present invention relates to crystalline salts of (S) 8-chloro-5-(5-bromo-2,3-dihydrobenzofuran-7-yl)-3-methyl-2,3,4,5-tetrahydro-1H-3-benzazepine-7-ol, their preparation and use as therapeutic agents.

International patent appl. No. WO 93/17012 discloses a class of compounds exhibiting strong antidopaminergic effects and thus making them useful in treatment of disorders in the central nervous system related to dysfunctions of the dopamine D-1 receptor system, e.g. psychosis, pain, depression and Parkinson's disease.

In example 1 of International appl. No. WO 93/17012 the preparation of (S)-8-chloro-5-(5-bromo-2,3-dihydrobenzofuran-7-yl)-3-methyl-2,3,4,5-tetrahydro-1H-3-benzazepine-7-ol of formula I is described:

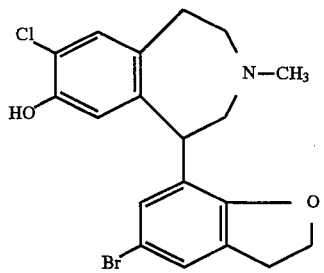

Because of its poor solubility, it is preferred that the compound of formula I is used as a therapeutic agent in the form of an acid addition salt.

Further, it has been found that some acid addition salts of the compound of formula I do form alternate polymorphic forms. This is pharmaceutically undesirable because of the potential that the salt occurs in more than one crystalline form making it very difficult to predict how the various parts of the body will react to the different crystalline forms.

In general, for commercial use it is important to have a physiologically acceptable salt with good bioavailability, good handling properties, and reproducible crystalline form.

Surprisingly, it has now been found that a series of new pharmaceutically acceptable acid addition salts of the compound of formula I, having the antidopaminergic effect corresponding to the basic compound, can be obtained in a reproducible crystalline form.

Accordingly, the present invention provides a series of crystalline salts of (S)-8-chloro-5-(5-bromo-2,3-dihydrobenzofuran-7-yl)-3-methyl-2,3,4,5-tetrahydro-1H-3-benzazepine-7-ol derived from organic acids such as fumaric, tartaric and mandelic acids.

Preferred salts of the invention are (S)-8-chloro-5-(5-bromo-2,3-dihydrobenzofuran-7-yl)-3-methyl-2,3,4,5-tetrahydro-1H-3-benzazepin-7-ol, hemifumarate; (S)-8-chloro-5-(5-bromo-2,3-dihydrobenzofuran-7-yl)-3-methyl2,3,4,5-tetrahydro-1H-3-benzazepin-7-ol, L(+)-hemitartrate; (S)-8-chloro-5-(5-bromo-2,3-dihydrobenzofuran-7-yl)-3-methyl-2,3,4,5-tetrahydro-1H-3-benzazepin-7-ol, D(−)-mandelate.

The acid addition salts of the (S) 8-chloro-5-(5-bromo-2,3-dihydrobenzofuran-7-yl)-3-methyl-2,3,4,5-tetrahydro-1 H-3-benzazepine-7-ol are prepared by dissolving the acid of the corresponding addition salt and the compound of formula I in a common solvent, and crystallizing the resulting salt from the solution.

Examples of the common solvents include lower aliphalic alcohols such as ethanol, methanol, 2-propanol, 2-butanol, 1-hexanol and solvents like isobutylmethylketone and tetrahydrofuran.

The present invention also provides pharmaceutical compositions comprising crystalline salts of (S) 8-chloro-5-(5-bromo-2,3-dihydrobenzofuran-7-yl)-3-methyl-2,3,4,5-tetrahydro-1H-3-benzazepine-7-ol and a pharmaceutically acceptable carrier.

The compositions of this invention are usually adapted for oral administration, but formulations for dissolution for parenteral administration are also within the scope of this invention.

The composition is usually presented as a unit dose composition containing 0.1–3000 mg of a compound in accordance with the invention for oral dosing. Typical dosage for antiphsychotic effect would vary between 1.0–1500 mg, preferably between 10–1000 mg per day either once or divided in 2 or 3 doses when administered orally.

Preferred unit dosage forms include in solid form, tablets or capsules, in liquid form, solutions, suspensions, emulsions, elixirs or capsules filled with the same, or in form of sterile injectable solutions.

The composition of this invention may be formulated by conventional methods of galenic pharmacy.

Conventional excipients are such pharmaceutically acceptable organic or inorganic carrier substances suitable for parenteral or oral application which do not deleteriously react with the active compound.

Examples of such carriers are water, salt solutions, alcohols, polyethylene glycols, polyhydroxyethoxylated castor oil, syrup, peanut oil, olive oil, gelatin, lactose, terra alba, sucrose, agar, pectin, acacia, amylose, magnesium stearate, talc, silicic acid, stearic acid, fatty acid monoglycerides and diglycerides, pentaerythritol fatty acid esters, hydroxymethylcellulose and polyvinylpyrrolidone.

The pharmaceutical preparations can be sterilized and mixed, if desired, with auxiliary agents, such as binders, lubricants, preservatives, disintegrants, stabilizers, wetting agents, emulsifiers, salt for influencing osmotic pressure, buffers and/or colouring substances and the like, which do not deleteriously react with the active compound.

For parenteral application, particularly suitable are injectable solutions or suspensions, preferably aqueous solutions with the active compound dissolved in polyhydroxylated castor oil.

For oral administration, particularly suitable are tablets, dragees, or capsules having talc and/or a carbohydrate carrier or binder or the like, the carrier preferably being lactose and/or corn starch and/or potato starch. A syrup, elixir or like can be used when a sweetened vehicle can be employed.

A typical tablet, which may be prepared by conventional tabletting techniques, contains:

| | |
|---|---|
| Active compound | 10 mg |
| Lactosum | 67.8 mg Ph.Eur. |
| Avicel ® | 31.4 mg |
| Amberlite ® IRP 88 | 1.0 mg |
| Magnesii stearas | 0.25 mg Ph.Eur. |

The invention also provides methods of treatment of certain disorders in the central nervous system related to dysfunctions of the dopamine D-1 receptor system, e.g. psychosis, such as schizophrenia including acute and chronic syndromes, depression, pain and Parkinson's disease in mammals including humans which methods comprises administering an effective amount of a pharmaceutically acceptable crystalline salt of (S)-8-chloro-5-(5-bromo-2,3-dihydrobenzofuran-7-yl)-3-methyl-2,3,4,5-tetrahydro-1H-3-benzazepine-7-ol.

The invention further provides pharmaceutically acceptable crystalline salts of (S)-8-chloro-5-(5-bromo-2,3-dihydrobenzofuran-7-yl)-3-methyl-2,3,4,5-tetrahydro-1H-3-benzazepine-7-ol for use in the treatment of disorders in the central nerveous system related to dysfunctions of the dopamine D-1 receptor system, e.g. psychosis, such as schizophrenia, including both positive and negative symptoms, depression, pain and Parkinson's disease.

The acid addition salts of (S)-8-chloro-5-(5-bromo-2,3-dihydrobenzofuran-7-yl)-3-methyl-2,3,4,5-tetrahydro-1H-3-benzazepine-7-ol of the invention were synthesized and crystallized from common solvents as described in the following examples.

EXAMPLE 1

(S)-8-chloro-5-(5-bromo-2,3-dihydrobenzofuran-7-yl)-3-methyl-2,3,4,5-tetrahydro-1H-3-benzazepin-7-ol, hemifumarate Fumaric acid (0.58 g, 5.0 mmol) was dissolved in 99% ethanol at reflux temperature. (S)-8-chloro-5-(5-bromo-2,3-dihydrobenzofuran-7-yl)-3-methyl-2,3,4,5-tetrahydro-1H-3-benzazepin-7-ol (2.04 g, 5.0 mmol) was added. The solution was cooled and stirred at room temperature. The resulting suspension was filtered. The filtercake was washed with 99% ethanol (3×5 ml), and dried in vacuo at 40° C.

Yield: 1.58 g (66%) of white crystalline product. M.p. by DSC 251° C.

Elemental Analysis: ($C_{21}H_{21}BrClNO_4$) Calculated: C 54.04 H 4.54 N 3.00% Found: C 53.90 H 4.62 N 2.85% Alternate polymorphic forms: No

EXAMPLE 2

(S)-8-chloro-5-(5-bromo-2,3-dihydrobenzofuran-7-yl)-3-methyl-2,3,4,5-tetrahydro-1H-3-benzazepin-7-ol, L(+)-hemitartrate The preparation was carried out analogously to the preparation in Example 1 using 5.0 mmol of the compound of formula I and L(+)-tartaric acid.

Yield: 1.45 g (60%). M.p. by DSC 249° C.

Elemental Analysis: ($C_2H_{22}BrClNO_5$): Calculated: C 52.14 H 4.58 N 2.90% Found: C 52.31 H 4.68 N 2.85% Alternate polymorphic form: No

EXAMPLE 3

(S)-8-chloro-5-(5-bromo-2,3-dihydrobenzofuran-7-yl)-3-methyl-2,3,4,5-tetrahydro-1H-3-benzazepin-7-ol, D(−)-mandelate The preparation was carried out analogously to the preparation in Example 1 using 5.0 mmol of the compound of formula I and D(−)-mandelic acid.

Yield: 1.63 g (58%). M.p. by DSC 204° C.

Elemental analysis: ($C_{27}H_{27}BrClNO_5$): Calculated: C 57.82 H 4.85 N2.50% Found: C 58.00 H 4.99 N 2.13% Alternate polymorphic form: No

We claim:

1. A fumaric acid and D(−)-mandelic acid crystalline salt of (S)-8-choro-5-(5-bromo-2,3,-dihydrobenzofuran-7-yl)-3-methyl-2,3,4,5-tetrahydro-1H-3-benzazepine-7-ol.

2. A crystalline salt according to claim 1 which is (S)-8-chloro-5-(5-bromo-2,3-dihydrobenzofuran-7-yl)-3-methyl-2,3,4,5-tetrahydro-1H-3-benzazepin-7-ol, hemifumarate; (S)-8-chloro-5-(5-bromo-2,3-dihydrobenzofuran-7-yl)-3-methyl-2,3,4,5-tetrahydro-1H-3-benzazepin-7-ol, D(−)-mandelate.

3. A pharmaceutical composition comprising a therapeutically effective amount of a crystalline salt according to claim 1 together with a pharmaceutically acceptable carrier or diluent.

4. The pharmaceutical composition according to claim 3 in the form of a dosage unit containing about 1.0–1500 mg of the active ingredients.

5. A method of treating a central nervous system disorder related to dysfunctions of the dopamine D-1 receptor system in a mammal comprising administering an effective amount of a crystalline salt according to claim 1.

6. A method of treating a central nervous system disorder related to dysfunctions of the dopamine D-1 receptor system in a mammal comprising administering an effective amount of a crystalline salt according to claim 1.

* * * * *